United States Patent [19]
Dai et al.

[11] Patent Number: 5,744,652
[45] Date of Patent: Apr. 28, 1998

[54] METHOD FOR THE MANUFACTURE OF METHYL TERTIARY BUTYL ETHER FROM TERTIARY BUTYL ALCOHOL AND METHANOL

[75] Inventors: Pei-Shing Eugene Dai; Laurence Darrel Neff; Kyle Lee Preston, all of Port Arthur; Rei-Yu Judy Hwan, Sugar Land, all of Tex.

[73] Assignee: Huntsman Specialty Chemicals Corp., Austin, Tex.

[21] Appl. No.: 815,984

[22] Filed: Mar. 10, 1997

[51] Int. Cl.⁶ .................................................. C07C 41/00
[52] U.S. Cl. ........................ 568/671; 568/697; 568/698
[58] Field of Search ........................... 568/671, 697, 568/698

[56] References Cited

U.S. PATENT DOCUMENTS

| | | | |
|---|---|---|---|
| 5,523,493 | 6/1996 | Cameron et al. | 568/671 |
| 5,559,275 | 9/1996 | Barger | 568/671 X |
| 5,563,301 | 10/1996 | Preston et al. | 568/698 |
| 5,659,090 | 8/1997 | Cameron et al. | 568/671 |

*Primary Examiner*—Paul F. Shaver
*Attorney, Agent, or Firm*—Russell R. Stolle; Ron D. Brown; Carl G. Ries

[57] ABSTRACT

Methyl tertiary butyl ether is prepared from TBA contaminated with oxygen-containing impurities by decomposing the impurities to gaseous products, by charging the thus-treated tertiary butyl alcohol and methanol to an etherification reactor to form an etherification reaction product, by distilling the etherification reaction product to provide a lower boiling fraction containing isobutylene, methanol and methyl tertiary butyl ether by charging the lower boiling fraction to a finishing reactor to react the isobutylene and methanol contained therein to from additional MTBE and by recovering MTBE from the etherification reaction product and the isobutylene conversion product.

18 Claims, 1 Drawing Sheet

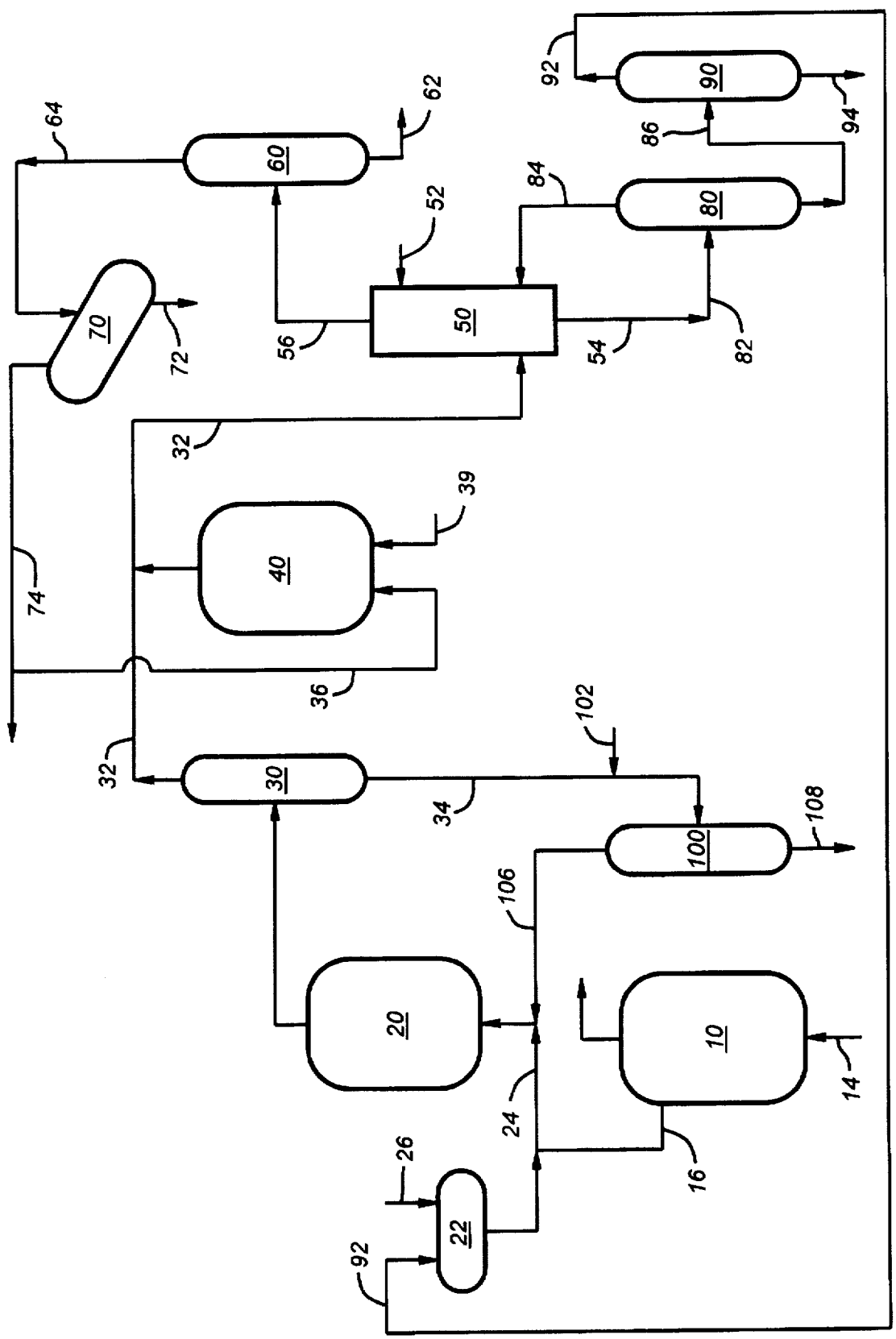

METHOD FOR THE MANUFACTURE OF METHYL TERTIARY BUTYL ETHER FROM TERTIARY BUTYL ALCOHOL AND METHANOL

BACKGROUND OF THE INVENTION

1. Technical Field of the Invention

This invention relates to a process for the manufacture of methyl tertiary butyl ether (MTBE) from tertiary butyl alcohol (TBA) and methanol (MeOH). More particularly, this invention relates to a process wherein TBA contaminated with oxygen-containing impurities is preliminarily charged to a decomposition reactor containing a bed of a copper catalyst to decompose the oxygen-containing impurities to non-condensible gases, whereby a portion of the TBA will be dehydrated to form isobutylene (IBTE), wherein isobutylene and TBA from the decomposition reactor are charged to an etherification reactor and reacted therein with MeOH to form MTBE and wherein unreacted TBA and IBTE are recovered and reacted to form additional MTBE.

Still more particularly, this invention relates to a process wherein TBA contaminated with oxygen-containing impurities including acidic impurities such as formic acid, methyl formate and tertiary butyl formate and peroxides such as tertiary butyl hydroperoxide, ditertiary butyl peroxide, etc., is charged to a decomposition reactor containing a bed of a copper chromite catalyst to decompose the oxygen-containing impurities to non-condensible gases, whereby a portion of the TBA will be dehydrated to form isobutylene and water, to the reaction of the thus-purified tertiary butyl alcohol and isobutylene with methanol in an etherification reactor to form an etherification reaction product comprising unreacted methanol, unreacted TBA, water, isobutylene and MTBE, to the distillation of the etherification reaction product in a first distillation column to provide a first lower boiling fraction comprising isobutylene, methanol and methyl tertiary butyl ether and a first higher boiling distillation fraction comprising methanol, tertiary butyl alcohol and water, to the reaction of the isobutylene and methanol in the first lower boiling fraction in a finishing reactor to form an isobutylene conversion product comprising methyl tertiary butyl ether, unreacted methanol, unreacted isobutylene and tertiary butyl alcohol, to the recovery unreacted tertiary butyl alcohol in the first higher boiling fraction and to recycle of the thus-recovered tertiary butyl alcohol to the etherification reactor.

2. Prior Art

In U.S. Pat. No. 4,144,138 (1979) to Rao et al., there is disclosed a method for manufacture of methyl tertiary butyl ether from tertiary butyl alcohol and methanol and for resolving the etherification reaction effluent by azeotropic distillation.

Kruse et al. U.S. Pat. No. 5,243,091 discloses a method for the preparation of methyl tertiary butyl alcohol wherein peroxides-contaminated tertiary butyl alcohol is passed through a peroxides-decomposition reactor to decompose the peroxides after which the peroxides-free tertiary butyl alcohol is catalytically reacted with methanol to form a reaction product that is separated into a lower boiling isobutylene distillation fraction comprising isobutylene, methanol and methyl tertiary butyl ether and a higher boiling distillation fraction comprising methanol, tertiary butyl alcohol and water, wherein the lower boiling isobutylene distillation fraction and a first recycle isobutylene fraction are reacted to forman isobutylene conversion product that is charged, together with recycle isobutylene to a methanol extraction zone and countercurrently contacted with water to provide an overhead raffinate comprising aqueous isobutylene, and wherein the isobutylene is recovered and recycled.

Gupta U.S. Pat. No. 5,292,964 discloses a method for the preparation of methyl tertiary butyl alcohol wherein a mixture of methanol and tertiary butyl alcohol is catalytically reacted to form a reaction product containing the water of etherification and at least one mol of methanol per two moles of methyl tertiary butyl ether, wherein the reaction product is fractionated to a lower boiling methanol and methyl tertiary butyl ether fraction from the water and tertiary butyl alcohol and wherein the methanol in the lower boiling distillation fraction is reacted with isobutylene to form additional methyl tertiary butyl ether.

Gupta states that it is essential to provide a reaction product containing at least one mol of methanol per two moles of methyl tertiary butyl ether, so that water is separable from the methyl tertiary butyl ether in the fractionating column to provide a lower boiling distillation fraction substantially free from water.

Grane et al. U.S. Pat. No. 4,296,262 is representative of patents directed to the manufacture and recovery of tertiary butyl alcohol by the thermal decomposition of tertiary butyl hydroperoxide.

Matouq et al. discuss a "COMBINED PROCESS FOR PRODUCTION OF METHYL TERT.-BUTYL ETHER FROM TERT.-BUTYL ALCOHOL AND METHANOL" at *Journal of Chemical Engineering of Japan*, Vol. 27, No. 3, 1994, pp. 301–306.

Another discussion of the formation of methyl tertiary butyl ether is found in a paper entitled "WHY METHYL TERT.BUTYL ETHER PRODUCTION BY REACTIVE DISTILLATION MAY YIELD MULTIPLE SOLUTIONS," *Ind. Eng. Chem. Res.* 1995, Vol. 34, pp. 987–991.

A study of the dehydration of tertiary butyl alcohol is disclosed in an article by Ohtsuka et al. entitled "STUDIES OF THE ACIDITY AND IONIC CONDUCTIVITY OF SILICA-SUPPORTED HETEROPOLY COMPOUNDS. I. THE DEHYDRATION OF t-BUTYL ALCOHOL OVER HETEROPOLY COMPOUND CATALYSTS," *Bull. Chem. Soc. Jpn.*, Vol. 62, 3195—3201 (1989).

The manufacture of isobutylene by the dehydration of tertiary butyl alcohol is also discussed by Abrahamet al. in a paper entitled "MAKE ISOBUTYLENE FROM TBA," *Hydrocarbon Processing*, February 1992, pp. 51–54.

Another paper discussing the dehydration of tertiary olefins by Kantam et al., entitled "MONTMORILLONITE CATALYZED DEHYDRATION OF TERTIARYALCOHOLS TO OLEFINS," is found in the *Tetrahedron Letters*, Vol. 34, No. 7, pp. 1185–1186 (1993).

Copper Chromite catalysts are described in, for example:

| U.S. Pat. No. |
| --- |
| 2,741,618 |
| 2,795,600 |
| 3,781,406 |
| 3,883,445 |
| 3,787,322 |

U.S. Pat. No. 3,855,388 describes a method of preparing an extruded copper chromite-alumina oxidation catalyst.

U.S. Pat. No. 4,666,879 describes an extruded copper chromite-alumina hydrogenation catalyst which is prepared by blending copper chromite and an extrudable alumina typically having a pseudoboehmite or an alpha-hydroxyboehite structure.

Copper chromate catalysts historically have been used in ester hydrogenolysis reactions to produce a variety of alcohol products. The reaction demands rather severe process conditions in terms of temperature and hydrogen pressure.

BACKGROUND OF THE INVENTION

Problems with Methyl Formate

In the operation of a plant to produce methyl tertiary butyl ether from TBA and MEOH one of the by-products is formic acid. This formic acid may react in downstream operations with methanol or t-butanol to form methyl formate (MeF) or t-butyl formate (TBF). The tertiary butyl alcohol feed to the MTBE reactors may contain as much as 0.4–1.3 wt. % of t-butyl formate. Tertiary butyl formate can be converted to methyl formate through a trans-esterification reaction with methanol in the MTBE reactor. In the acidic medium, methyl formate is hydrolyzed to form formic acid and methanol. Formic acid causes severe corrosion problems in carbon steel vessels which are present in some plants. Methyl formate is irreversibly converted to formate salt in a basic medium.

One method of addressing this problem is to neutralize methyl formate by the injection of a strong base such as, for example, KOH or NaOH. The problem with this method is that the potassium or sodium formate, thus formed, is disposed into a waste water stream and the residual caustic in the waste water stream can catalyze a number of undesirable side reactions to generate C7–C11 ketones from acetone.

It would represent a distinct advance in the art if there were a method available for removing methyl formate and peroxide impurities from tertiary butanol and MTBE streams in a manner such that these chemicals would not be just neutralized, but would be completely broken down to noncondensible gas products, such as hydrogen, carbon monoxide, carbon dioxide, and methane as well as liquid products such as TBA, MeOH, and isobutylene.

A high degree of removal of formate would reduce consumption of caustic, reduce the potential for corrosion problems caused by formates, alleviate the problem of having high total organic content in the waste water stream and thereby permit a PO/MTBE plant to run at full design capacity.

The process of this invention is distinguished from the prior art technology for hydrogenolysis of formic esters in that no hydrogen is fed into the reactor. The decomposition of TBF and DTBP leads to the formation of non-condensible gas products including CO, $CO_2$, $H_4$. The dehydration of TBA gives isobutylene and water. No isobutane was ever detected in the gas products indicating that hydrogenation reaction does not take place in this process. The process chemistry may be best presented as follows:

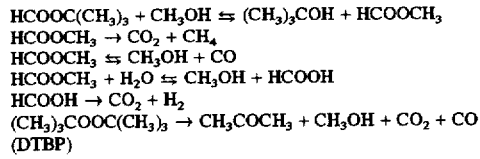

SUMMARY OF THE INVENTION AND DESCRIPTION OF PREFERRED EMBODIMENTS

This invention relates to a process comprising the steps of:

a) feeding a TBA charge stock contaminated with oxygen-containing impurities such as peroxides and formates, to a reactor containing a bed of a copper decomposition catalyst to decompose the oxygen-containing contaminants, to dehydrate a portion of the TBA to form isobutylene (IBTE) and water, and to provide a liquid TBA feedstock comprising tertiary butyl alcohol, isobutylene and water and a gaseous off-gas reaction product, b) charging the liquid TBA feedstock to an etherification reactor together with methanol to forman etherification reaction product comprising unreacted methanol, unreacted TBA, water, isobutylene and MTBE, c) charging the etherification reaction product to a first distillation column and fractionating it therein to form a first lower boiling fraction comprising unreacted isobutylene, methyl tertiary butyl ether, unreacted methanol and water and a first higher boiling fraction comprising unreacted tertiary butyl alcohol and water, d) charging the first lower boiling fraction to a water-washing tower for countercurrent contact with water to form a raffinate comprising MTBE, isobutylene and water and an extract comprising MTBE, methanol and water, e) charging the raffinate to a third distillation column and separating it therein into a third higher boiling MTBE product fraction and a third lower boiling aqueous isobutylene fraction, f) separating the lower boiling aqueous isobutylene fraction into a water fraction and an isobutylene recycle fraction, g) charging to isobutylene recycle fraction and added methanol to a finishing reactor containing a bed of an etherification catalyst and reacting them therein to form a finishing reactor product containing additional methyl tertiary butyl ether, and h) recovering methyl tertiary butyl ether from the third higher boiling MTBE product fraction and the finishing reactor product.

A preferred embodiment of the present invention includes the additional steps of:

i) charging the extract from the water washing tower to a fourth distillation column and separating it therein into a fourth lower boiling MTBE fractionand a fourth higher boiling aqueous methanol fraction, j) recycling the fourth lower boiling MTBE fraction to the water washing tower, and k) separating methanol from the water in the fourth higher boiling aqueous methanol fraction and recycling the separated methanol to the etherification reactor.

In accordance with a further embodiment of the present invention, l) the first higher boiling distillation fraction from the first distillation column is charged to a second distillation column and separated therein into a second lower boiling fraction comprising tertiary butyl alcohol and a second higher boiling fraction comprising water, and m) the second lower boiling fraction is recycled to the etherification reactor.

DETAILED DESCRIPTION OF THE PRESENT INVENTION DECOMPOSITION OF OXYGEN-CONTAINING IMPURITIES

It is known to prepare tertiary butyl alcohol by the thermal or catalytic decomposition of tertiary butyl hydroperoxide. It is also known to prepare tertiary butyl alcohol by the catalytic reaction of tertiary butyl hydroperoxide with propylene to form propylene oxide and tertiary butyl alcohol. The tertiary butyl alcohol feedstock derived from tertiary butyl hydroperoxide in this manner will contain oxygen-containing impurities such as peroxides and formates. A typical feedstock prepared in this fashion will contain from about 95 to 99 wt. % of tertiary butyl alcohol and less than about 2.0 wt. % of oxygen-containing impurities such as peroxides and formates, i.e., tertiary butyl hydroperoxide, ditertiary butyl peroxide, allyl tertiary butyl peroxide, etc., and formate contaminants such as formic acid, methyl formate, tertiary butyl formate, etc.

The Decomposition Reactor

In accordance with the MTBE manufacture and purification method of the present invention, a tertiary butyl alcohol charge stock contaminated with oxygen-containing contaminants including peroxides and formates is charged to a decomposition reactor containing a bed of a copper catalyst to decompose the oxygen-containing impurities to non-condensible gases, whereby a portion of the TBA will be dehydrated to form isobutylene.

The Copper Decomposition Catalyst

A copper decomposition catalyst is used in the practice of the present invention which will optionally contain one or more metals selected from Group IIA and Group VIII.

In particular, a catalyst is preferred comprising from 20 to 80% by weight copper chromite, optionally containing 20 to 80% by weight of at least one extrudable inorganic binder.

These copper-chromite catalysts are generally prepared by a process comprising:

a. Preparing a blend comprising from about 20 to about 80% by weight of copper chromite, from about 20 to about 80% by weight of at least one extrudable inorganic binder material, from about 1 to about 10% by weight, preferably from about 3 to about 7% by weight, based on the weight of the binder, of a peptizing agent, and sufficient water to forman extrudable blend, b. Extruding the blend to form an extrudate, and c. Calcining the extrudate. (See U.S. Pat. No. 5,124,295, incorporated by reference herein in its entirety.

The preferred copper chromite catalyst utilized in the present invention comprises a commercially available, unsupported copper chromite. One example of a commercially available copper chromite catalyst is sold by Engelhard as Cu-1180P. It is a powdered barium-stabilized catalyst useful in slurry phase hydrogenation, having the typical composition 43% CuO, 45% $Cr_2O_3$ and 9% BaO. Another commercially available copper chromite catalyst from Engelhard is designated Cu-1160P, having a typical composition of 43% CuO, 45% $Cr_2O_3$ and 9% BaO.

The above blends of copper chromite and inorganic binder materials may be formed by extruding the blends in known extrusion equipment, and the blends may be extruded into any number of shapes and sizes. For example, the blends can be extruded into a trilobe such as that described in U.S. Pat. No. 4,517,077; a cylindrical shape with a hollow interior and one or more reinforcing ribs such as described in U.S. Pat. Nos. 4,510,263 and 4,089,941; rectangular and triangular shaped tubes such as those described in U.S. Pat. No. 4,441,990; cloverleaves, cross, and C-shapes such as those described in U.S. Pat. No. 3,764,565, etc.

The extrudates which are obtained from any of the above extrusion methods may be dried at temperatures up to 200° C. and thereafter calcined at temperatures of 350° C. or higher. Generally, calcination temperatures of from about 375° to about 475° or 500° C. are utilized. Some of the properties of the catalysts of the present invention are affected by the calcination temperature and calcination atmosphere. For example, higher surface areas generally are obtained at lower calcination temperature and by shorter exposure of the extrudate to higher temperatures.

Following calcination, but before use, the catalyst may be and is normally activated by reducing at least some of the copper chromite and the copper oxide present in the catalyst. The reduction step may be carried out in situ immediately prior to use, or, alternatively, reduction may be carried out in advance of use by contacting the catalyst with hydrogen or a mixture of hydrogen and nitrogen at elevated temperatures according to well-known procedures in which a portion or all of the copper oxide and copper chromite are reduced.

The reduced catalyst may then be stabilized or passivated, e.g., by exposing the catalyst to air or $CO_2$ to form a thin oxide layer on the surface, or the reduced catalyst may be stored in a protective medium such as an inert liquid until use.

The surface area of the catalyst of this invention can be increased by lowering the temperature at which the extrudate is calcined or by reducing the time of calcination at higher temperatures. Surface area of the catalyst can also be increased by using higher surface area binder materials, appropriate extrusion aids and/or peptizing agents.

The total pore volume of the pores in the catalyst of the present invention may be increased by increasing the water content of the extrudable blend so long as the blend remains extrudable and the extrudate maintains its physical integrity. The total pore volume also can be controlled and increased by using lower density binders, extruders such as the twin screw extruder with appropriate die and extrusion pressure. Extrusion aids such as organic materials may be included in the extrudable blends. Since these organics burnout on calcination of the extrudate, the resulting catalyst will have a higher total pore volume.

DECOMPOSITION REACTOR OPERATING CONDITIONS

The reaction conditions to be utilized when decomposing oxygen-containing impurities in the presence of a copper decomposition catalyst include a reaction temperature of about 250° to about 500° F., a pressure of about 100 to about 600 psi and a liquid hourly space velocity (LHSV) of about 0.1 to about 10.

The Etherification Reaction Catalyst

In accordance with the MTBE manufacture and purification method of the present invention, an etherification reactor containing a bed of etherification catalyst is utilized. A preferred catalyst is a sulfonic acid resin etherification catalyst such as a sulfonated polystyrene resin cross-linked with divinyl benzene.

Any suitable solid resin etherification catalyst may be used for this purpose, such as a strongly acidic ion exchange resin consisting essentially of sulfonated polystyrene, such as a divinyl benzene crosslink polystyrene matrix containing from about 0.5 to about 20% of copolymerized divinyl benzene. Resins of this nature are manufactured and sold commercially under various trade names such as "Dowex 50," "Dowex M-31," "Dowex M-32," "Nalcite HCR," "Amberlyst A-15" and "Amberlyst A-16." The use of catalyst of this nature is disclosed, for example, in Rao U.S. Pat. No. 4,144,138.

A wide variety of supported phosphorus acid-type catalysts can be used, such as Kieselguhr impregnated with phosphoric acid as disclosed in Frolich U.S. Pat. No. 2,282,469, titania having phosphoric acid impregnated thereon as disclosed in Knifton U.S. Pat. No. 4,822,921, a hetero polyacid such as 12-tungstophosphoric acid or 12-molybdophosphoric acid supported on titania, etc.

Zeolites, as disclosed in Japanese Patent 0007432, or aluminosilicate zeolites, as disclosed in Chang et al. U.S. Pat. No. 4,058,576, may also be used.

The reaction conditions to be utilized when reacting methanol with tertiary butyl alcohol in the presence of a sulfonic acid resin etherification catalyst of the type disclosed in the prior art include a reaction temperature of about 90° to about 140° C., a pressure of about 30 to about 500 psia and a space velocity of about 0.5 to about 20 volumes of feed per volume of etherification catalyst per hour.

The Finishing Reactor

In accordance with the present invention, isobutylene is obtained during the recovery process and is brought into contact with a solid resin etherification catalyst together with methanol in a finishing reactor, in order to convert a significant portion of the isobutylene and methanol to methyl tertiary butyl ether.

Any suitable solid resin etherification catalyst may be used for this purpose, such as a strongly acidic ion exchange resin consisting essentially of sulfonated polystyrene, such as a divinyl benzene crosslink polystyrene matrix containing from about 0.5 to about 20% of copolymerized divinyl benzene. Resins of this nature are manufactured and sold commercially under various trade names such as "Dowex 50," "Dowex M-31," "Dowex M-32," "Nalcite HCR," "Amberlyst A-15" and "Amberlyst A-16." The use of catalyst of this nature is disclosed, for example, in Rao U.S. Pat. No. 4,144,138.

The isobutylene is brought into contact with the solid resin etherification catalyst in the finishing reactor (that can also be considered an isobutylene conversion reactor) under conversion conditions including, for example, a temperature of about 35° to about 13020 C., a pressure of about 30 to about 500 psia and a contact time of about 0.5 to about 20 volumes of IBTE per volume of etherification catalyst per hour. As a consequence, an isobutylene conversion product is formed which will normally contain from about 0 to about 10 wt. % of isobutylene, about 75 to about 85 wt. % of methyl tertiary butyl ether and from about 10 to about 15 wt. % of methanol and about 0 to about 2 wt. % of tertiary butyl alcohol.

BRIEF DESCRIPTION OF THE DRAWING

The drawing is a schematic flow sheet with conventional parts omitted showing the general reaction and recovery sequence of the present invention for the manufacture and purification of methyl tertiary butyl ether.

DESCRIPTION OF THE PREFERRED EMBODIMENT

Turning now to the drawing, there is shown a schematic flow sheet illustrating the preferred method for the practice of the process of the present invention. In the drawing, conventional parts, such as valves, pumps, temperature control sensors, pressure sensors, heaters, coolers, flow control regulation apparatus, reflux condenses, reboilers, etc., have been omitted.

In accordance with the present invention, there is provided a decomposition reactor 10 containing a bed of a copper decomposition catalyst, such as a copper chromite decomposition catalyst.

The contaminated tertiary butyl alcohol feedstock is charged by way of a tertiary butyl alcohol feed line 14 to decomposition reactor 10 which is operated at a reaction temperature of about 250° to about 500° F. (about 120° to about 260° C.), a pressure of about 100 to about 600 psi and a liquid hourly space velocity (LHSV) of about 0.1 to about 10.

Within the decomposition reactor 10, the peroxide contaminants will be decomposed to form water and tertiary butyl alcohol, and trace amounts of other decomposition products such as acetone. The formates will be decomposed to form gaseous decomposition products including carbon monoxide, water, carbon dioxide, etc. The tertiary butyl alcohol will be partially dehydrated to form isobutylene and water.

The gaseous decomposition products are discharged from the decomposition reactor 10 by a line 18 and the liquid reaction products are discharged by a line 16 leading to an etherification reactor 20 together with methanol which is charged by a line 24. The flow of methanol through the lines 24 is regulated so that a molar excess of methanol is present in the line 16 leading to the etherification reactor 20, such as, for example, a molar ratio of about 1.1 to about 3 moles of methanol per mol of tertiary butyl alcohol charged by line 16.

Within the etherification reactor 20, the etherification feed mixture is brought into contact with the bed of etherification catalyst, such as a sulfonic acid resin etherification catalyst under reaction conditions including a pressure of about 30 to about 500 psia, and more preferably from about 200 to about 300 psia, a temperature of about 30° to about 200° C., and more preferably from about 70° to about 140° C., and still more preferably from about 80° to about 120° C. When the catalyst is a supported phosphorus acid-type catalyst, clay, modified clay, etc., the reaction temperature may suitably be in the range of about 150° to about 190° C.

Contact time within the etherification reaction zone is suitably such that about 0.5 to about 20 volumes of feed mixture per volume of etherification catalyst per hour are fed to the etherification reaction zone 20 and, more preferably from about 1 to about 4 volumes of feed mixture per volume of etherification catalyst per hour.

Within the etherification reaction zone 20, methanol will exothermically react with the tertiary butyl alcohol and isobutylene to form methyl tertiary butyl ether which will be contained in a reaction product discharged from the etherification reactor 20 by way of a line 28 leading to a first methyl tertiary butyl ether (MTBE) distillation column 30.

As a specific example, when the solid etherification catalyst is a sulfonic acid resin such as Amberlyst 15 and when the molar ratio of methanol to tertiary butyl alcohol in the feed mixture charged to the etherification reactor 20 by the line 16 is within the ratio of about 2.0 moles of methanol per mole of isobutylene and tertiary butyl alcohol, and the reaction is conducted at a temperature of about 100° C. at a feed rate of about 2.0 volumes of feed mixture per volume of catalyst per hour, the etherification reaction product may have the composition in part shown by the following table:

| ETHERIFICATION REACTION PRODUCT | |
|---|---|
| Component | % |
| Water | 13.7 |
| Methanol | 27.6 |
| Isobutylene | 3.5 |
| TBA[1] | 14.1 |
| MTBE[2] | 34.5 |
| Other[3] | 6.6 |

[1]Tertiary butyl alcohol
[2]Methyl tertiary butyl ether
[3]May include acetone, propanol, ditertiary butyl peroxide, tertiary butyl formate, etc.

The etherification reaction product charged to the first distillation zone 30 by way of the charge line 28 is fractionated therein under distillation conditions including a liquid reflux temperature of about 40° to about 80° C., a reflux ratio of about 1.0 to about 1.5, a reboiler temperature of about 95° to about 105° C., and a pressure of about 15 to about 60 psia, the distillation condition being selected such that substantially all of the MTBE in the etherification reaction product 20 is taken overhead from the first distillation zone 30 by a line 32 and such that substantially all of the water exits the distillation zone by the line 34. As a consequence, the first lower boiling distillation fraction 32 taken overhead from the distillation zone 30 will be substantially anhydrous and will comprise substantially all of the isobutylene and substantially all of the methyl tertiary butyl ether and some of the methanol charged to the first distillation zone 30. The first higher boiling impure methanol distillation fraction 34 discharged from the second MTBE distillation zone 30 will comprise methanol, tertiary butyl alcohol and water.

The first higher boiling aqueous TBA fraction discharged from the distillation column 30 by a line 106 leading to a second distillation column 100. The higher boiling aqueous TBA fraction 18 will normally contain minor amounts of acidic by-products formed in the etherification reactor 20 and in order to prevent and/or inhibit corrosion in the first distillation column 100, a neutralizing agent such as sodium hydroxide, potassium hydroxide, etc., is added to the line 18 by a line 102 in an amount sufficient to neutralize the acidic by-products.

The higher boiling aqueous TBA fraction 18 is separated in the second distillation column 100 into a second lower boiling TBA fraction 106 for recycle to the etherification reactor 10 and a second higher boiling water fraction 108.

In accordance with the present invention, the first lower boiling distillation fraction 32 is charged byway of charge line 36 to a methanol solvent extraction tower 50 at a point adjacent the bottom thereof where it is countercurrently contacted with water introduced into the solvent extraction tower 50 by a charge line 52.

Within the methanol solvent extraction tower 50, solvent extraction conditions are established for countercurrent solvent extraction including a ratio of isobutylene to water within the range of about 0.8 to about 1.8 volumes of isobutylene per volume of water per hour, and more preferably a ratio of about 1.0 to about 1.5 volumes of isobutylene per volume of water. Extractive conditions to be established may suitably include a temperature of about 20° to about 60° C., and more preferably from about 30° to about 40° C., and a pressure of about 50 to about 500 psia, and more preferably from about 50 to about 150 psia.

As a consequence, a supernatant raffinate will be formed which is withdrawn from the methanol solvent extraction tower 50 by line 56 leading to a third distillation column 60. The extract is discharged from the solvent extraction tower 50 by way of a bottoms charge line 54 leading to a fourth methyl tertiary butyl ether distillation column 80.

Within the third methyl tertiary butyl ether purification distillation column 60, distillation conditions are established including a liquid reflux temperature of about 30° to about 60° C., and more preferably from about 40° to about 55° C., a reboiler temperature of about 100° to about 140° C., and more preferably from about 125° to about 135° C. and a pressure of about 70 to about 120 psia, and more preferably from about 90 to about 110 psia, to thereby form a third lower boiling aqueous isobutylene distillation fraction 64 discharged from the third distillation column 60 and a third higher boiling methyl tertiary butyl ether product distillation fraction 62 consisting essentially of product, namely methyl tertiary butyl ether.

The third aqueous isobutylene distillation fraction 64 will comprise a mixture of isobutylene and water and is suitably charged to a decantation zone 70 where it can settle to form a supernatant isobutylene phase withdrawn from the decantation zone 70 byway of a line 74. Water is discharged in the decantation zone 70 by way of a water discharge line 72 and is suitably purged from the system.

The extract 54 charged to the fourth distillation column 80 will comprise methyl tertiary butyl ether, methanol and water, and is suitably fractionated therein under distillation conditions including a liquid reflux temperature of about 30° to about 90° C. and more preferably from about 50° to about 75° C., and a reboiler temperature of about 80° to about 120° C., and more preferably from about 105° to about 115° C. and a pressure of about 15 to about 60 psia, and more preferably from about 40 to about 50 psia, to form a fourth lower boiling methyl tertiary butyl ether recycle distillation fraction 84 comprising methyl tertiary butyl ether which may suitably be charged to the methanol solvent extraction tower 50. A fourth higher boiling aqueous methanol distillation fraction comprising water and methanol is discharged from the fourth distillation column 80 by a line 86 leading to a fifth distillation column 90. The distillation fraction 86 charged to the fifth methanol distillation column 90 is fractionated therein under distillation conditions which may suitably include a liquid reflux temperature of about 30° to about 80° C., and more preferably from about 60° to about 75° C. a reboiler temperature of about 100° to about 140° C., and more preferably from about 110° to about 120° C., and a pressure of about 15 to about 60 psia, and more preferably from about 20 to about 30 psia, into a fifth lower boiling methanol distillation fraction 92 which may be suitably charged to a charge drum 22 together with fresh methanol charged by a line 26. A fifth higher boiling aqueous distillation fraction consisting essentially of water is discharged from the fifth methanol distillation column 90 by way of a line 94 and may be discharged from the system.

The isobutylene in the line 74 is suitably recycled to an isobutylene finishing reactor 40 together with excess methanol charged by a line 39. The finishing reactor 40 will contain a bed of solid resin etherification catalyst such as a bed of Amberlyst 15 sulfonated polystyrene-divinyl benzene copolymer acidic ion exchange resin.

Etherification reaction conditions are established in the isobutylene finishing reactor 40 including, for example, a temperature of about 35° to about 130° C., and more preferably from about 40° to about 90° C., a pressure of about 50 to about 500 psia, and more preferably from about 150 to about 250 psia, and a contact time of about 0.5 to about 4 volumes of first distillation fraction per volume of solid resin etherification catalyst per hour. As a consequence, a portion of the methanol and isobutylene contained in the first distillation fraction 32 will be converted to methyl tertiary butyl ether. Typically, the conversion will amount to about 20 to about 85 wt. %, based on the isobutylene.

Thus, an isobutylene conversion product is formed, which is discharged in the isobutylene conversion reactor 40 by a line 42 leading to a methanol solvent extraction tower 50.

The composition of a representative feedstock and a representative isobutylene conversion product may be characterized as follows:

| ISOBUTYLENE FEEDSTOCK AND CONVERSION PRODUCT | | |
|---|---|---|
| Component | Feed, wt. % | Product, wt. % |
| Water | 0.5 wt. % | 0.4 wt. % |
| Methanol | 13.5 wt. % | 8.0 wt. % |
| Isobutylene | 12.0 wt. % | 2.5 wt. % |
| TBA | 0.9 wt. % | 1.0 wt. % |
| MTBE | 70.4 wt. % | 85.5 wt. % |
| Other | 2.7 wt. % | 2.6 wt. % |

EXAMPLES

The catalysts employed in Examples I–VI were commercially available from Engelhard, United Catalysts Inc. (UCI), and Calsicat.

The process of catalytic removal of formates and peroxides was conducted using a fixed-bed downflow reactor made of ⅝" OD×17" long stainless steel tubing. 11 cc of catalyst granules having 20–30 mesh sizes was loaded into the center zone of catalyst bed in the reactor. The feedstock used in the catalyst screening is the tertiary bull alcohol (TBA) obtained from a TBA Day Tank of a PO/MTBE plant, which contains typically Bout 0.2–1.2 wt % tertiary bull formate (TBF) and Bout 0.1–1.0 wt % organic peroxides.

The catalyst granules were dried at 200°–600° F. for 2 hours in a stream of nitrogen gas at a rate of 50 cc/min prior to contacting with the feed. The liquid feed rate was varied from 11 to 33 cc/hr (LHSV=1–3). The feed was pumped under 300 psi back pressure. The TBA feed and nitrogen were mixed and preheated at 120°–180° F. before entering the reactor. The reactor temperature was either maintained at constant level while LHSV was varied or raised from 200° to 500° F. when LHSV was fixed at one. The typical test conditions are: nitrogen feed rate 50 cc/min; TBA feed rate 11 cc/min (LHSV=1; 300° F.; and 300 psi). The preferred process temperature and pressure are 250°–500° F. and 100–600 psi. During the 48-hour test period samples of reactor effluent were withdrawn and the compositions were analyzed by gas chromatography.

The copper-chromite catalyst of this invention permits the attainment of >90% formate removal and >95% peroxide removal. Catalysts containing binary or ternary basic oxide components such as CaO, ZnO, MgO and alumina and optionally have Cu loading in the range of 10–40 wt % can also be employed.

Practice of the method of this invention will be apparent to those skilled in the art from the following examples. The examples are only for illustration and the invention is not intended to be limited thereby.

EXPERIMENTAL

Unsupported copper-chromite catalysts containing small amounts of metals from Group IIA and VII were tested and compared with control catalysts.

Typical chemical and physical properties of the copper chromite catalysts used in the examples can be characterized as follows:

TABLE I

| Typical Chemical and Physical Properties | | | | |
|---|---|---|---|---|
| | Cu-1986T | E-106T | G-98 | Cu-0891 |
| Copper content as Cu, Wt % | 35 | 33.5 | 39 | 23.2 |
| Chromium content as Cr, Wt % | 30 | 27.4 | 37 | 27.1(Zn) |
| Barium content as Ba, Wt % | 3 | 7.2 | | 7.3(Al) |
| Manganese content as Mn, Wt % | | 0 | 3 | |
| Crush strength, Lt. | 14 | 15 | | 27.6 |
| Surface area, m₂/g | 55 | 90 | | |
| Pore Volume, cc/g | 0.03 | 0.18 | | 0.15 |
| Bulk density, Lbs/Ft₃ | | 95 | | |
| Packed A.B.D., g/cc | 1.6 | | | 1.72 |

Alumina supported CuO/ZnO catalyst used for comparison were obtained from Engelhard under the designation Cu-0891. Two binary basic oxide carriers, C125-1-02 comprising 50 wt % CuO, 25 wt % ZnO, and 25 wt % bentonite clay and C125-1-01 containing 25 wt % CuO, 50 wt % ZnO and clay balance, were provided by UCI.

The best results were obtained using the unsupported copper chromite catalysts demonstrated in Examples I, III and IV. The catalysts of these examples were obtained from Engelhard, UCI and Calsicat, respectively. The results in Tables II, IV and V show that the activities of these catalysts for TBF conversions follow the order of Engelhard Cu-1986 (Example I) is greater than Calsicat E-106 TU (Example IV) is greater than UCI-G-89 (Example III).

The supported catalyst from Engelhard, Cu-0891 (Example II) showed good TBF removal and DTBP decomposition, but the conversion was low.

Experimental catalyst 052-95-2584-000 comprised 85% CuO and 15% clay. This catalyst was prepared by dissolving 11.75 grams of copper nitrate, $Cu(NO_3)_2 \cdot 2.5H_2O$, and 1.30 grams of nickel nitrate, $Ni(NO_3)_2 \cdot 6H_2O$ in distilled water for a total volume of 20 ml. Then 50 grams of support was impregnated with the solution at room temperature, dried at 120° C. for two hours and calcined at 425° C. for 3 hours and 538° C. for about one hour.

Experimental catalyst 052-95-2584-000 comprised 50% CuO, 25% Zn, and 25% clay, C125-1-02. This catalyst was prepared by dissolving 11.75 grams of copper nitrate, $CU(NO_3)_2 \cdot 2.5H_2O$, and 1.30 grams of nickel nitrate, $Ni(NO_3)_2 \cdot 6H_2O$ in distilled water for a total volume of 20 ml. Then 50 grams of support was impregnated with the solution at room temperature, dried at 120° C. for two hours and calcined at 427° C. for 3 hours and 538° C. for about one hours.

Experimental catalyst 052-95-6949-224 comprised 25% CuO, 50% ZnO, and 25% clay. This catalyst was prepared by dissolving 11.75 grams of copper nitrate, $Cu(NO_3)_2 \cdot 2.5H_2O$ and 1.30 grams of nickel nitrate, $Ni(NO_3)_2 \cdot 6H_2O$ in distilled water for a total volume of 20 ml. Then 50 grams of support was impregnated at room temperature, dried at 120° C. for two hours and calcined at 427° C. for 3 hours and 538° C. for 1 hour.

The data for Example I, demonstrating decomposition over Engelhard CU-1986 copper chromite catalyst, is summarized in Table II.

The TBA feed contains at least three kinds of formate esters, namely, 0.63% tertiary butyl formate (TBF), 0.031% isopropyl formate (IFP), and 0.32% isobutyl formate (IBF). The feed also contains 0.53% di-tertiary butyl peroxide (DTBP) and 0.36% secondary butyl acetate (SBA). The conversion for all five components are shown in Table I. It is seen that TBF removal greater than 90% can be attained at temperatures higher than 306° F. Complete removal of DTBP can also be achieved. Over the temperature range of 200°–500° F., the TBA dehydration is below 15%.

The saponification number (SAP No.), expressed in units of mg KOH/g sample, is the amount of caustic required to neutralize the free acids and organic esters. The SAP No. at pH=11 of the products obtained with Example I, shown in Table I, was reduced to as low as 1.06 from 7.83 for the TBA feed. If the organic formates were simply converted to free formic acid, there should not be any reduction in the SAP No. of the products. The results indicate that both formates and free acids are decomposed to non-acidic materials.

TABLE II

Data Summary of Formate Decomposition Over
Copper Chromite Catalyst at Various Temperature
Catalyst ID: 052-95-2577, Engelhard Cu Chromite
Run No.: 094-95-0028-000
Run Date: 7-26-95

| Bed Temperature (F.) | TBA Conversion (Wt %) | TBF Removal (Wt %) | DTBP Removal (Wt %) | Weight Percent Recovery (%) | SAP No. pH = 11 | SAP No. pH = 7 |
|---|---|---|---|---|---|---|
| 188 | 7.34 | 46.69 | 28.30 | 93.67 | 4.07 | 3.77 |
| 233 | 9.15 | 55.92 | 35.45 | 92.25 | 4.08 | 2.78 |
| 280 | 5.23 | 82.82 | 90.90 | 94.84 | 1.53 | 0.83 |
| 306 | 0.12 | 95.97 | 100.00 | 98.52 | 1.06 | 0.36 |
| 325 | 2.48 | 96.93 | 100.00 | 96.76 | 1.40 | 0.73 |
| 351 | 10.28 | 95.96 | 100.00 | 91.00 | 1.45 | 0.70 |

The data for formate decomposition over another copper chromite catalyst, Cu-0891 from Engelhard, is summarized in Table III.

TBF removal greater than 90% can be obtained at temperatures greater than 379° F. The catalyst also showed high degrees of DTBP decomposition (>95%) at reactor temperatures above 379° F. This CuO/ZnO/alumina catalyst exhibited a TBA conversion less than 30% in the entire temperature range of 200°–500° F.

TABLE III

Data Summary of Formate Decomposition Over
Catalyst at Various Temperatures
Catalyst ID: 052-95-2578-000, Cu-0891
Run No.: 094-95-0021-000
Run Date: 7-10-95

| Bed Temperature (F.) | TBA Conversion (Wt %) | TBF Removal (Wt %) | DTBP Removal (Wt %) | Weight Percent Recovery (%) |
|---|---|---|---|---|
| 186 | 9.7 | 87.1 | 29.5 | 91.7 |
| 234 | 22.7 | 85.1 | 66.5 | 81.9 |
| 351 | 21.6 | 70.3 | 78.5 | 82.7 |
| 379 | 0 | 97.1 | 96.1 | 99.0 |
| 428 | 13.4 | 98.6 | 100.00 | 88.3 |
| 477 | 25.5 | 96.9 | 100.00 | 79.5 |

The data from Examples I, III and IV, for the copper chromite catalyst obtained from Engelhard, United Catalysts Inc. (UCI) and Calsicat, respectively, are compared in Tables II, IV and V for their TBF, DTBP and TBA conversions.

The results clearly show that the activities of these catalysts for TBF conversion follow the order of Engelhard Cu-1986 (Example I)>Calsicat E-106 TU (Example IV)>UCI G-89 (Example III). The products obtained with Example I have the lowest SAP No. among the three types of copper chromite catalysts.

TABLE IV

Data Summary of Formate Decomposition Over
Copper Chromite Catalyst at Various Temperatures
Catalyst ID: 052-95-2592-000, Cu Chromite with MnO₂
Run No.: 094-95-0033-000
Run Date: 8-7-95

| Bed Temperature (F.) | TBA Conversion (Wt %) | TBF Removal (Wt %) | DTBP Removal (Wt %) | Weight Percent Recovery (%) | SAP No. pH = 11 | SAP No. pH = 7 |
|---|---|---|---|---|---|---|
| 188 | 55.9 | 42.4 | 50.6 | 87.6 | | |
| 235 | 8.5 | 23.8 | 41.9 | 93.4 | | |
| 283 | 3.3 | 92.0 | 99.0 | 96.6 | 2.1 | 0.1 |
| 300 | 7.9 | 80.7 | 100.00 | 93.2 | 2.6 | 1.4 |
| 329 | 9.9 | 76.8 | 100.00 | 91.5 | 3.4 | 2.1 |
| 352 | 11.3 | 83.1 | 98.7 | 90.3 | 3.4 | 2.8 |

TABLE V

Data Summary of Formate Decomposition Over
Copper Chromite Catalyst at Various Temperatures
Catalyst ID: 052-95-2589-000, Calsicat E-106TU
Run No.: 094-95-0036-000
Run Date: 8-14-95

| Bed Temperature (F.) | TBA Conversion (Wt %) | TBF Removal (Wt %) | DTBP Removal (Wt %) | Weight Percent Recovery (%) | SAP No. pH = 11 | SAP No. pH = 7 |
|---|---|---|---|---|---|---|
| 191 | 57.6 | 58.4 | 45.8 | 45.8 | | |
| 236 | 5.80 | 68.6 | 77.6 | 77.6 | | |
| 285 | 11.6 | 97.8 | 100.00 | 100.00 | 2.52 | 1.10 |
| 309 | 4.50 | 91.3 | 100.00 | 100.00 | 2.99 | 1.77 |
| 330 | 4.70 | 91.1 | 100.00 | 100.00 | 3.36 | 1.45 |
| 354 | 7.30 | 95.9 | 100.00 | 100.00 | 3.87 | 2.12 |

The data summary on formate decomposition for UCI's catalyst C-125-1-02 comprising 50% CaO, 25% Zno, and 25% bentonite clay, is presented in Table VI. The carrier contains 75% of binary basic oxide components (CaO and ZnO). Greater than 90% TBF removal can be obtained at temperatures as low as 191° F. DTBP removal increases with increasing temperature, and at 373° F. it reaches 92.8%. TBA dehydration remains lower than 20% at temperatures up to 373° F.

TABLE VI

Data Summary of Formate Decomposition Over
Copper Catalyst at Various Temperatures
Catalyst ID: 052-95-2584-000, 50% CaO, 25% ZnO, 25% Clay
Run No.: 095-95-0007-000
Run Date: 8-16-95

| Bed Temperature (F.) | TBA Conversion (Wt %) | TBF Removal (Wt %) | DTBP Removal (Wt %) | Weight Percent Recovery (%) |
|---|---|---|---|---|
| 191 | 0.0 | 93.2 | 3.5 | 114.9 |
| 242 | 10.9 | 100.00 | 34.5 | 90.8 |
| 298 | 16.6 | 100.00 | 62.2 | 86.3 |
| 320 | 12.6 | 100.00 | 60.0 | 89.3 |

TABLE VI-continued

| | | | | |
|---|---|---|---|---|
| 341 | 13.2 | 100.00 | 73.5 | 88.8 |
| 373 | 12.9 | 100.00 | 92.8 | 89.0 |

The performance of Example VI, 6% Cu, 0.5% Ni catalyst on a UCI's carrier comprising 25% CaO, 50% ZnO and 25% bentonite clay, is presented in VII. 52.6% TBF conversion and 79.4% DTBP conversion were obtained at 356° F., and LHSV=1. The performance of Example VI is much inferior to the copper chromite catalysts of Examples I, III, and IV.

TABLE VII

Data Summary of Formate Decomposition Over
Copper Catalyst at Various Temperatures
Catalyst ID: 052-95-6949-224, 6% Cu, 0.5% Ni on
25% CaO/50% ZnO/25% Clay
Run No.: 094-95-0035-000
Run Date: 8-10-95

| Bed Temperature (F.) | TBA Conversion (Wt %) | TBF Removal (Wt %) | DTBP Removal (Wt %) | Weight Percent Recovery (%) |
|---|---|---|---|---|
| 191 | 71.6 | 31.2 | 1.0 | 108.1 |
| 238 | 2.4 | 33.1 | 13.6 | 97.7 |
| 286 | 9.5 | 52.9 | 30.8 | 92.1 |
| 309 | 5.8 | 51.2 | 51.9 | 94.7 |
| 332 | 8.4 | 46.3 | 54.9 | 92.8 |
| 356 | 5.7 | 52.6 | 79.4 | 94.7 |

The results of catalytic activities for decomposition of TBF and DTBP present in TBA feed are summarized in Table VIII. Examples I–V are catalysts of this invention, and Examples VI-XI control catalysts. It is seen that the catalysts of this invention are superior to the control catalysts for both TBF and DTBP decomposition. There is a distinct difference between Calsicat's and UCI's MgO catalysts, particularly in the TBF conversion.

TABLE VIII

RESULTS OF CATALYST EVALUATION FOR DECOMPOSITION OF
TBF AND DTBP IN TBA FEED SCREENING OF
CATALYST SUPPORTS

| Catalyst | Temp. °F. | TBF | DTBP | TBA |
|---|---|---|---|---|
| Engelhard Cu-1986T | 374 | 96 | 100 | 10 |
| EXAMPLE I | 282 | 83 | 91 | 5 |
| | 188 | 47 | 28 | 7 |
| Engelhard Cu-0891 | 370 | 97 | 96 | 0 |
| EXAMPLE II | 282 | 70 | 79 | 22 |
| | 189 | 87 | 30 | 10 |
| UCI G-89 CuCr w/MnO$_2$ | 378 | 83 | 99 | 11 |
| EXAMPLE III | 284 | 92 | 99 | 3 |
| | 189 | 42 | 51 | 56 |
| Caliscat E-106TU | 379 | 96 | 100 | 7 |
| EXAMPLE IV | 285 | 98 | 100 | 12 |
| | 188 | 58 | 46 | 5 |
| CaO/ZnO/Clay | 373 | 100 | 92.8 | 12.9 |
| C125-1-02 | 298 | 100 | 62.2 | 16.6 |
| EXAMPLE V | 191 | 100 | 3.5 | 0 |
| CuNi/CaO/ZnO/Clay | 356 | 53 | 79 | 6 |
| EXAMPLE VI | 286 | 53 | 31 | 10 |
| | 191 | 31 | 1 | 72 |
| UCI MgO | 377 | 23 | 68 | 5 |
| EXAMPLE VII | 283 | 18 | 25 | 5 |
| | 188 | 26 | 28 | 11 |
| Calsicat MgO | 377 | 90 | 83 | 11 |
| EXAMPLE VIII | 284 | 58 | 54 | 8 |

TABLE VIII-continued

RESULTS OF CATALYST EVALUATION FOR DECOMPOSITION OF
TBF AND DTBP IN TBA FEED SCREENING OF
CATALYST SUPPORTS

| Catalyst | Temp. °F. | TBF | DTBP | TBA |
|---|---|---|---|---|
| | 188 | 40 | 26 | 7 |
| Norton ZrO$_2$ | 379 | 69 | 93 | 8 |
| EXAMPLE IX | 285 | 55 | 50 | 15 |
| | 191 | 100 | 38 | 13 |
| TK-753 γ/Al$_2$O$_3$ | 374 | 65 | 92 | 14 |
| EXAMPLE X | 283 | 55 | 31 | 6 |
| | 188 | 59 | 13 | 8 |
| HTC-400 θ/Al$_2$O$_3$ | 374 | 67 | 98 | 4 |
| EXAMPLE XI | 277 | 47 | 30 | 4 |
| | 189 | 52 | 23 | 5 |

Reaction Conditions: TBA Day-Tank Feed, LHSV 1.0, 300 psi

We claim:

1. A process for the preparation of methyl tertiary butyl ether from methanol and a tertiary butyl alcohol charge stock contaminated with oxygen-containing impurities including peroxides and formates which comprise the steps of:
   a) feeding the tertiary butyl alcohol charge stock to a reactor containing a bed of a copper decomposition catalyst to decompose the oxygen-containing contaminants, to dehydrate a portion of the TBA to form isobutylene (IBTE) and water, and to provide a liquid TBA charge stock comprising tertiary butyl alcohol, isobutylene and water and a gaseous off-gas reaction product,
   b) feeding the liquid TBA charge stock to an etherification reactor together with methanol to form an etherification reaction product comprising unreacted methanol, unreacted TBA, water, isobutylene and MTBE.

2. A method as in claim 1 wherein the catalyst in the decomposition reactor is a copper catalyst containing a metal selected from Group IIA and Group VIII of the periodic table.

3. A method as in claim 2 wherein the catalyst in the decomposition reactor is a copper chromite catalyst.

4. A method as in claim 2 wherein the catalyst in the decomposition reactor is a barium stabilized copper chromite catalyst containing about 43% CuO, about 45% Cr$_2$O$_3$ and 9% BaO.

5. A process for the preparation of methyl tertiary butyl ether from methanol and a tertiary butyl alcohol charge stock contaminated with oxygen-containing impurities including peroxides and formates which comprise the steps of:
   a) feeding the tertiary butyl alcohol charge stock to a reactor containing a bed of a copper decomposition catalyst to decompose the oxygen-containing contaminants, to dehydrate a portion of the TBA to form isobutylene (IBTE) and water, and to provide a liquid TBA charge stock comprising tertiary butyl alcohol, isobutylene and water and a gaseous off-gas reaction product,
   b) feeding the liquid TBA charge stock to an etherification reactor together with methanol to form an etherification reaction product comprising unreacted methanol, unreacted TBA, water, isobutylene and MTBE.
   c) charging the etherification reaction product to a first distillation column and fractionating it therein to form a first lower boiling fraction comprising unreacted isobutylene, methyl tertiary butyl ether, unreacted methanol and water and a first higher boiling fraction comprising unreacted tertiary butyl alcohol and water, d) charging the first lower boiling fraction to a water-washing tower for countercurrent contact with water to form a raffinate comprising MTBE, isobutylene and water and an extract comprising MTBE, methanol and water, e) charging the raffinate to a second distillation column and separating it therein into a second higher boiling MTBE product fraction and a second lower boiling aqueous isobutylene fraction, f) separating the lower boiling aqueous isobutylene fraction into a water fraction and an isobutylene recycle fraction, g) charging the isobutylene recycle fraction and added methanol to a finishing reactor containing a bed of an etherification catalyst and reacting them therein to form a finishing reactor product containing additional methyl tertiary butyl ether, and h) recovering methyl tertiary butyl ether from the second higher boiling MTBE product fraction and the finishing reactor product.

6. A method as in claim 5 including the additional steps of:

i) charging the extract from the water washing tower to a third distillation column and separating it therein into a third lower boiling MTBE fraction and a third higher boiling aqueous methanol fraction, j) recycling the third lower boiling MTBE fraction to the water washing tower, and k) separating methanol from the water in the third higher boiling aqueous methanol fraction and recycling the separated methanol to the etherification reactor.

7. A method as in claim 6 including the additional steps of:

l) charging the first higher boiling distillation fraction from the first distillation column to a fourth distillation column and separated therein into a fourth lower boiling fraction comprising tertiary butyl alcohol and a fourth higher boiling fraction comprising water, and m) the fourth lower boiling fraction is recycled to the etherification reactor.

8. A process for the preparation of methyl tertiary butyl ether from methanol and a tertiary butyl alcohol charge stock contaminated with oxygen-containing impurities including peroxides and formates which comprise the steps of:

a) feeding the tertiary butyl alcohol charge stock to a reactor containing a bed of a copper decomposition catalyst to decompose the oxygen-containing contaminants, to dehydrate a portion of the TBA to form isobutylene (IBTE) and water, and to provide a liquid TBA feedstock comprising tertiary butyl alcohol, isobutylene and water and a gaseous off-gas reaction product, b) charging the liquid TBA feedstock to an etherification reactor together with methanol to form an etherification reaction product comprising unreacted methanol, unreacted TBA, water, isobutylene and MTBE, c) charging the etherification reaction product to a first distillation column and fractionating it therein to form a first lower boiling fraction comprising unreacted isobutylene, methyl tertiary butyl ether, unreacted methanol and water and a first higher boiling fraction comprising unreacted tertiary butyl alcohol and water, d) charging the first lower boiling fraction to a water-washing tower for countercurrent contact with water to form a raffinate comprising MTBE, isobutylene and water and an extract comprising MTBE, methanol and water, e) charging the raffinate to a second distillation column and separating it therein into a second higher boiling MTBE product fraction and a second lower boiling aqueous isobutylene fraction, f) separating the lower boiling aqueous isobutylene fraction into a water fraction and an isobutylene recycle fraction, g) charging the isobutylene recycle fraction and added methanol to a finishing reactor containing a bed of an etherification catalyst and reacting them therein to form a finishing reactor product containing additional methyl tertiary butyl ether, and h) recovering methyl tertiary butyl ether from the second higher boiling MTBE product fraction and the finishing reactor product, i) charging the extract from the water washing tower to a third distillation column and separating it therein into a third lower boiling MTBE fraction and a third higher boiling aqueous methanol fraction, j) recycling the third lower boiling MTBE fraction to the water washing tower, k) separating methanol from the water in the third higher boiling aqueous methanol fraction and recycling the separated methanol to the etherification reactor, l) charging the first higher boiling distillation fraction from the first distillation column to a fourth distillation column and separated therein into a fourth lower boiling fraction comprising tertiary butyl alcohol and a fourth higher boiling fraction comprising water, and m) the fourth lower boiling fraction is recycled to the etherification reactor.

9. A method as in claim 8 wherein the methanol and the tertiary butyl alcohol feedstock are charged to the methyl tertiary butyl ether etherification reactor in the molar ratio of about 1.1 to about 3.0 moles of methanol per combined mole of tertiary butyl alcohol and isobutylene in the tertiary butyl alcohol feedstock.

10. A method as in claim 8 wherein the etherification catalysts in the methyl tertiary butyl ether etherification zone and in the finishing reactor are solid resin divinyl benzene cross-linked sulfonated polystyrene catalysts.

11. A method as in claim 8 wherein the methanol is reacted with the tertiary butyl alcohol and isobutylene in the etherification reactor under conversion conditions including a temperature of about 80° C. to about 120° C. and a pressure of about 30 to 500 psia at a flow rate of about 0.5 to 20 volumes of feed mixture per volume of etherification catalyst per hour, and wherein the isobutylene reaction mixture is reacted in the finishing reactor under reaction conditions including a temperature of about 35° to about 130° C., a pressure of about 50 to 500 psia and a flow rate of about 0.5 to about 4 volumes of reaction mixture per volume of catalyst per hour.

12. A method as in claim 8 wherein the said etherification reaction product is distilled in the second distillation column under distillation conditions including a liquid reflux temperature of about 40° to about 80° C., a reflux ratio of about 1.0 to about 1.5, a reboiler temperature of about 95° to about 105° C., and a pressure of about 15 to about 60 psia.

13. A method as in claim 12 wherein the distillation conditions are selected to provide a lower boiling distillation fraction comprising about 70 to 80 wt. % of methyl tertiary butyl ether, about 10 to 20 wt. % of methanol, about 5 to 15 wt. % of isobutylene and about 0.05 to about 2 wt. % of water.

14. A method as in claim 8 wherein the catalyst in the decomposition reactor is a clay-supported copper catalyst comprising about 85 wt. % CuO.

15. A method as in claim 8 wherein the catalyst in the decomposition reactor is a clay-supported copper catalyst comprising about 25 wt. % CuO, about 50 wt. % ZnO.

16. A method as in claim 8 wherein the catalyst in the decomposition reactor is a copper catalyst containing a metal selected from Group IIA and Group VIII of the periodic table.

17. A method as in claim 8 wherein the catalyst in the decomposition reactor is a copper chromite catalyst.

18. A method as in claim 8 wherein the catalyst in the decomposition reactor is a barium stabilized copper chromite catalyst containing about 43% CuO, about 45% $Cr_2O_3$ and 9% BaO.

* * * * *